(12) United States Patent
Hirayama et al.

(10) Patent No.: US 7,555,937 B2
(45) Date of Patent: Jul. 7, 2009

(54) SAMPLE INJECTION DEVICE, SAMPLE INJECTION METHOD, AND LIQUID CHROMATOGRAPH

(75) Inventors: Aya Hirayama, Yokohama (JP); Osamu Shirota, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 249 days.

(21) Appl. No.: 11/795,153

(22) PCT Filed: Jan. 20, 2006

(86) PCT No.: PCT/JP2006/000887
§ 371 (c)(1),
(2), (4) Date: Jul. 12, 2007

(87) PCT Pub. No.: WO2006/077985
PCT Pub. Date: Jul. 27, 2006

(65) Prior Publication Data
US 2008/0229809 A1 Sep. 25, 2008

(30) Foreign Application Priority Data
Jan. 24, 2005 (JP) ............................. 2005-015583

(51) Int. Cl.
*G01N 30/24* (2006.01)
(52) U.S. Cl. .................................................. 73/61.55
(58) Field of Classification Search ............... 73/61.55, 73/863.33
See application file for complete search history.

(56) References Cited

U.S. PATENT DOCUMENTS

| | | | | |
|---|---|---|---|---|
| 4,811,611 A | * | 3/1989 | Uffenheimer | ............ 73/864.22 |
| 5,316,954 A | * | 5/1994 | Hupe et al. | .................... 436/89 |
| 5,738,783 A | * | 4/1998 | Shirota et al. | ............ 210/198.2 |
| 6,063,283 A | * | 5/2000 | Shirota et al. | ............... 210/656 |
| 7,175,812 B2 | * | 2/2007 | Tatsumi | ...................... 422/100 |
| 7,195,229 B2 | * | 3/2007 | Maeda | ........................ 251/205 |
| 2004/0175833 A1 | * | 9/2004 | Tatsumi | ....................... 436/49 |

FOREIGN PATENT DOCUMENTS

| | | |
|---|---|---|
| JP | 62-176756 | 11/1987 |
| JP | 2705582 | 12/1994 |
| JP | 10-010103 | 1/1998 |
| JP | 2002-228668 | 8/2002 |

* cited by examiner

*Primary Examiner*—Hezron Williams
*Assistant Examiner*—Rodney T Frank
(74) *Attorney, Agent, or Firm*—IPUSA, PLLC

(57) ABSTRACT

The present invention relates to a sample injection device, a sample injection method, and a liquid chromatograph that control the flow of a mobile phase using a switching valve. The sample injection device includes a port connected to a separation column, a pump for supplying a mobile phase, first and second sample injection needles, a syringe, and a valve configured to selectively connect the first sample injection needle to the pump or the syringe and to connect the second sample injection needle to the pump. When the first sample injection needle is attached to the port, the first sample injection needle is connected to the pump through operation of the valve. When the second sample injection needle is attached to the port, the first sample injection needle is connected to the syringe and the second sample injection needle is connected to the pump.

5 Claims, 11 Drawing Sheets

FIG.10

| | COMPARATIVE EXAMPLE | | EXAMPLE |
|---|---|---|---|
| THEORETICAL PLATE TP (JP) | 7659 | IMPROVEMENT ⇧ | 8686 |
| RETENTION TIME (RT) | 3.653 | | 3.611 |
| 5% PEAK WIDTH | 0.2374 | | 0.2201 |
| SKEWNESS | 1.26 | | 1.24 |

EXAMPLE

| | |
|---|---|
| TEST 1 | 0.0008 |
| TEST 2 | 0.0010 |
| TEST 3 | 0.0011 |
| TEST 4 | 0.0009 |
| AVERAGE | 0.0009 |

⇑ IMPROVEMENT

COMPARATIVE EXAMPLE

| | |
|---|---|
| TEST 1 | 0.0018 |
| TEST 2 | 0.0023 |
| TEST 3 | 0.0019 |
| TEST 4 | 0.0021 |
| AVERAGE | 0.0020 |

# SAMPLE INJECTION DEVICE, SAMPLE INJECTION METHOD, AND LIQUID CHROMATOGRAPH

TECHNICAL FIELD

The present invention generally relates to a sample injection device, a sample injection method, and a liquid chromatograph. More particularly, the present invention relates to a sample injection device, a sample injection method, and a liquid chromatograph that control the flow of a mobile phase using a switching valve.

BACKGROUND ART

In a liquid chromatograph, a sample is pressurized together with a liquid used as a mobile phase and sent to a column. Components of the sample are separated in the column, eluted, and then detected by a detector. A typical liquid chromatograph includes a mobile phase reservoir for holding a liquid used as a mobile phase, a mobile phase deaerator for removing air from the liquid mobile phase, a pump for feeding the liquid mobile phase from the mobile phase reservoir to a detector, a sample injection device for injecting a sample into the liquid mobile phase being sent to a separation column, the separation column filled with a filler for separating components of the sample, a constant-temperature bath for maintaining the separation column at a substantially constant temperature, and a detector for detecting eluted components of the sample.

A sample injection device of a liquid chromatograph has a switching valve, for example, as disclosed in patent document 1. The disclosed switching valve is configured to allow a sample to be drawn into a sample injection needle when drawing the sample into the sample injection needle and to allow the sample drawn into the sample injection needle to be sent to a column along with a flow of a mobile phase when the sample injection needle is attached to a sample injection port. FIG. 1 is a drawing illustrating an exemplary sample injection device.

The exemplary sample injection device shown in FIG. 1 includes a sample injection needle 100 (100A through 100C), a pump 103, a syringe 111, a wash liquid pump 112, a valve 113, a sample container 114, an injection valve (switching valve) 115, a cleaning device 120, a sample injection port 124, and a needle moving unit (not shown).

The injection valve 115 has six ports to which the sample injection needle 100, the mobile phase pump 103, the valve 113, the cleaning device 120, and the sample injection port 124 are connected. The injection valve 115 switches between a connection mode (connection mode A) indicated by solid lines A in FIG. 1 and a connection mode (connection mode B) indicated by broken lines B in FIG. 1.

Before analysis of a sample is started, the injection valve 115 is in the connection mode A and the sample injection needle 100 is attached to the sample injection port 124 (the sample injection needle 100 in this position is indicated by the reference number 100A) The sample injection needle 100A is connected via the injection valve 115 to the pump 103. The sample injection port 124 is connected via piping 125 and the injection valve 115 to a separation column 105. Accordingly, in the connection mode A, a mobile phase supplied from the pump 103 is fed into the separation column 105 via the sample injection needle 100A, the sample injection port 124, the piping 125, and the injection valve 115.

On the other hand, when drawing a sample into the sample injection needle 100, the injection valve 115 is switched to the connection mode B and the sample injection needle 100 is inserted into the sample container 114 (the sample injection needle 100 in this position is indicated by the reference number 100B). In the connection mode B, the sample injection needle 100B is connected to the syringe 111 via the injection valve 115 and the valve 113. Therefore, the sample in the sample container 114 can be drawn into the sample injection needle 100B by operating the syringe 111. Also, in the connection mode B, the pump 103 is connected via the injection valve 115 to the separation column 105 and therefore the mobile phase continues to be supplied to the separation column 105 even when the sample is being drawn into the sample injection needle 100.

When feeding the sample drawn into the sample injection needle 100 to the separation column 105, the sample injection needle 100 is inserted into a cleaning unit 117B and then into a cleaning unit 117A of the cleaning device 120 to clean its outer surface. New supplies of a wash liquid are continuously supplied to the cleaning units 117A and 117B of the cleaning device 120 by connecting the valve 113 to the wash liquid pump 112 at specified timings. Excess wash liquid is discharged from a waste liquid port 123.

Then, the cleaned sample injection needle 100 is inserted into the sample injection port 124 and the injection valve 115 is switched again to the connection mode A. As a result, the mobile phase supplied from the pump 103 to the sample injection needle 100A pushes the sample out of the sample injection needle 100A into the sample injection port 124. The sample is then carried by the flow of the mobile phase via the piping 125 and the injection valve 115 to the separation column 105. Thus, in the conventional sample injection device, a sample is sent from the sample injection needle 100A to the separation column 105 through the injection valve 115.

[Patent document 1] Japanese Patent Application Publication No. 10-010103

DISCLOSURE OF INVENTION

Problems to be Solved by the Invention

Meanwhile, with the improvement of detection sensitivity of liquid chromatographs configured as described above, a problem called "carry-over" has arisen. Carry-over is a problem where a substance in a previously analyzed sample remains in a liquid chromatograph and the remaining substance is detected in a subsequent analysis as if the substance originally exists in the sample used in the subsequent analysis. Thus, carry-over reduces the credibility of analysis results.

When a sample is injected into a liquid used as a mobile phase by a sample injection device, a portion of the sample may adhere to a metal and/or a resin in the sample injection device and remain in the device. Carry-over occurs if the remaining sample is introduced into the analysis system of a liquid chromatograph when a new sample is injected.

In the conventional sample injection device described above, the wash liquid pump 112, the valve 113, the cleaning device 120 are provided to clean the outer surface of the sample injection needle 100 after drawing in a sample, to clean the inner surface of the sample injection needle 100 after injecting the sample, and thereby to prevent the sample from remaining in the sample injection device. Although such a configuration can reduce carry-over to a certain extent, it is not effective enough to perform a high-precision analysis.

Means for Solving the Problems

A general object of the present invention is to provide a sample injection device, a sample injection method, and a liquid chromatograph that substantially obviate one or more problems caused by the limitations and disadvantages of the related art.

A more particular object of the present invention is to provide a sample injection device, a sample injection method, and a liquid chromatograph that can effectively reduce carry-over.

To achieve the above objects of the present invention, a sample injection device includes a sample injection port connected to a column; a mobile phase supplying unit configured to supply a mobile phase; a first sample injection needle attachable to the sample injection port; a second sample injection needle attachable to the sample injection port; a sample-suctioning unit connectable to the first sample injection needle and configured to draw a sample into the first sample injection needle when connected thereto; and a switching valve configured to selectively connect the first sample injection needle to the mobile phase supplying unit or the sample-suctioning unit and to connect the second sample injection needle to the mobile phase supplying unit; wherein the switching valve is configured to connect the first sample injection needle to the mobile phase supplying unit when the first sample injection needle is attached to the sample injection port, and configured to connect the first sample injection needle to the sample-suctioning unit and to connect the second sample injection needle to the mobile phase supplying unit when the second sample injection needle is attached to the sample injection port.

According to the above invention, when the first sample injection needle is attached to the sample injection port, the switching valve is switched to connect the first sample injection needle to the mobile phase supplying unit. As a result, the mobile phase from the mobile phase supplying unit is fed into the column via the first sample injection needle and the sample injection port.

On the other hand, when the second sample injection needle is attached to the sample injection port, the switching valve is switched to connect the first sample injection needle to the sample-suctioning unit and to connect the second sample injection needle to the mobile phase supplying unit. As a result, the mobile phase from the mobile phase supplying unit is fed into the column via the second sample injection needle and the sample injection port. Also, since the first sample injection needle is connected to the sample-suctioning unit, the sample can be drawn into the first sample injection needle by operating the sample-suctioning unit.

With the above configuration where the first or second sample injection needle can be selectively attached to the sample injection port, the column can be isolated from the switching valve. In other words, the above configuration makes it possible to constantly feed the mobile phase into the column from the first or second sample injection needle connected to the mobile phase supplying unit without connecting the column to the switching valve. This in turn makes it possible to feed a sample into the column without making the sample go through the switching valve by attaching the first sample injection needle containing the sample to the sample injection port and thereby to prevent the sample from remaining in the switching valve as with a conventional sample injection device.

The sample injection device of the present invention may also include a valve disposed in the path of piping connecting the second sample injection needle and the switching valve and configured to block the piping when the second sample injection needle is detached from the sample injection port.

The valve provided in the path of piping connecting the second sample injection needle and the switching valve prevents leakage of the mobile phase from the second sample injection needle when the second sample injection needle is detached from the sample injection port.

To achieve the above objects of the present invention, a method of injecting a sample into a column using the sample injection device described above includes a first step of attaching the first sample injection needle to the sample injection port, connecting the first sample injection needle via the switching valve to the mobile phase supplying unit, and disconnecting the second sample injection needle; a second step of drawing the sample into the first sample injection needle by connecting the first sample injection needle via the switching valve to the sample-suctioning unit, attaching the second sample injection needle to the sample injection port, and connecting the second sample injection needle via the switching valve to the mobile phase supplying unit; and a third step of attaching the first sample injection needle to the sample injection port, feeding the sample drawn into the first sample injection needle into the column by connecting the first sample injection needle via the switching valve to the mobile phase supplying unit, and disconnecting the second sample injection needle.

In the first step of the above method, the first sample injection needle is attached to the sample injection port and, at the same time, connected to the mobile phase supplying unit via the switching valve. Therefore, the mobile phase is fed into the column via the first sample injection needle. In this step, the second sample injection needle is disconnected from other components and is not used.

In the second step, the second sample injection needle connected via the switching valve to the mobile phase supplying unit is attached to the sample injection port. Therefore, the mobile phase is fed into the column via the second sample injection needle. Also, since the first sample injection needle is connected via the switching valve to the sample-suctioning unit, the sample can be drawn into the first sample injection needle.

In the third step, the first sample injection needle containing the drawn-in sample is attached to the sample injection port and, at the same time, connected to the mobile phase supplying unit via the switching valve. Therefore, the sample is fed into the column without going through the switching valve. This makes it possible to prevent a sample from remaining in the switching valve as with a conventional method.

In the above method of the present invention, a valve may be provided in the path of piping connecting the second sample injection needle and the switching valve and the piping may be blocked by the valve in the first and third steps.

With this configuration, the piping connecting the second sample injection needle and the switching valve is blocked by the valve when the second sample injection needle is not attached to the sample injection port so as to prevent leakage of the mobile phase from the second sample injection needle.

According to the present invention, a liquid chromatograph may include a sample injection port connected to a column; a mobile phase supplying unit configured to supply a mobile phase; a first sample injection needle attachable to the sample injection port; a second sample injection needle attachable to the sample injection port; a sample-suctioning unit connectable to the first sample injection needle and configured to draw a sample into the first sample injection needle when connected thereto; a switching valve configured to selectively connect the first sample injection needle to the mobile phase supplying unit or the sample-suctioning unit and to connect the first sample injection needle to the mobile phase supplying unit; a separation column into which the mobile phase and the sample are fed from the first sample injection needle and which is configured to separate components of the sample; and a detector configured to detect the components of the sample separated by the separation column; wherein the switching valve is configured to connect the first sample injection needle to the mobile phase supplying unit when the first sample injection needle is attached to the sample injection port, and configured to connect the first sample injection needle to the sample-suctioning unit and to connect the second sample injection needle to the mobile phase supplying unit when the second sample injection needle is attached to the sample injection port.

This configuration makes it possible to feed a sample into the column without making the sample go through the switching valve by attaching the first sample injection needle containing the drawn-in sample to the sample injection port, and thereby to prevent the sample from remaining in the switching valve as with a conventional liquid chromatograph. Thus, the liquid chromatograph of the present invention makes it possible to reduce carry-over and thereby to improve the accuracy of sample analysis.

Advantageous Effect of the Invention

The present invention makes it possible to prevent a sample from remaining in a switching valve and thereby to sufficiently reduce carry-over. Also, according to the present invention, a sample is sent from an injection port to the inlet of a column without going through a switching valve. This configuration makes it possible to minimize the diffusion of a sample and thereby to increase the number of theoretical plates of a detected peak.

BRIEF DESCRIPTION OF THE DRAWINGS

FIG. 10 is a table used to describe advantageous effects of the present invention (1)

EXPLANATION OF REFERENCES

Figure 1:
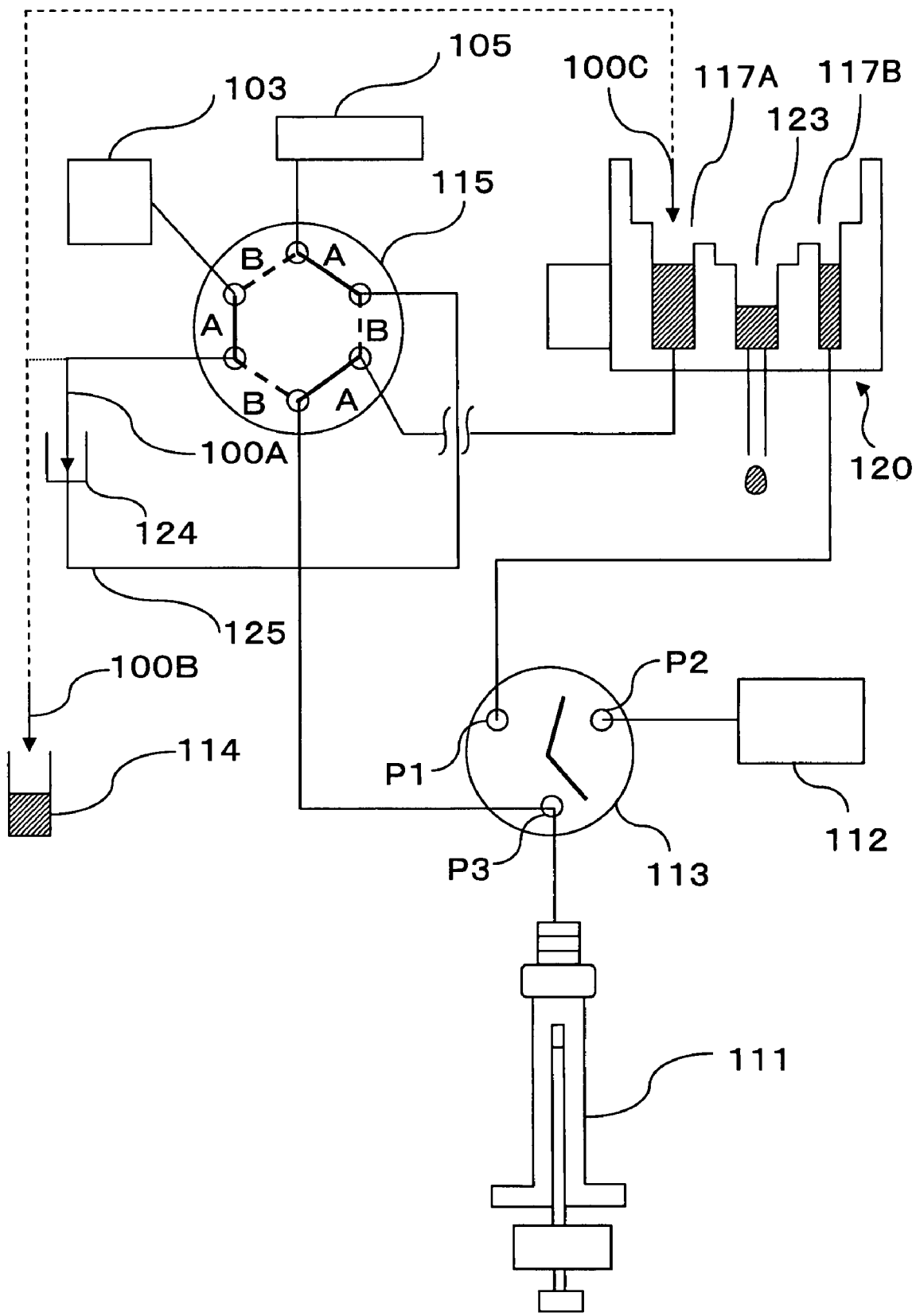
FIG. 1 is a schematic diagram illustrating an exemplary sample injection device.

1 Sample injection device
10A, 10B Sample injection needle
11 Syringe
12 Wash liquid pump
13 Valve
14 Sample container
15 Injection valve
17A, 17B Cleaning unit
18 Wash liquid container
19 Injection port
20 Cleaning device
26 Drip-preventing three-way solenoid valve
30 Liquid chromatograph
31 Mobile phase reservoir
32 Mobile phase deaerator
33 Pump
35 Separation column

BEST MODE FOR CARRYING OUT THE INVENTION

The best mode for carrying out the invention is described based on the following embodiments with reference to the accompanying drawings.

Figure 2:
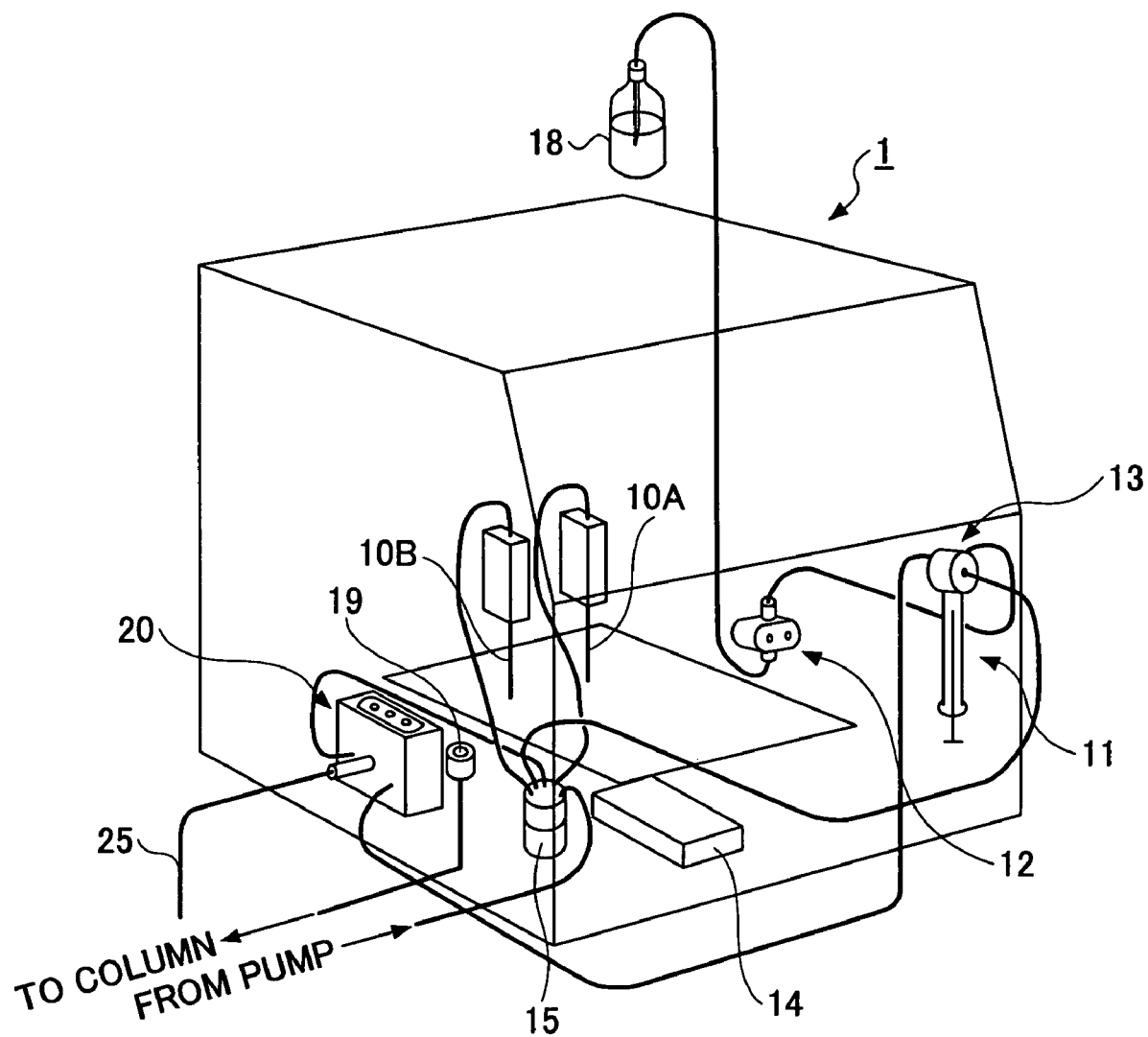
FIG. 2 is a schematic diagram illustrating a sample injection device according to an embodiment of the present invention.
Figure 3:
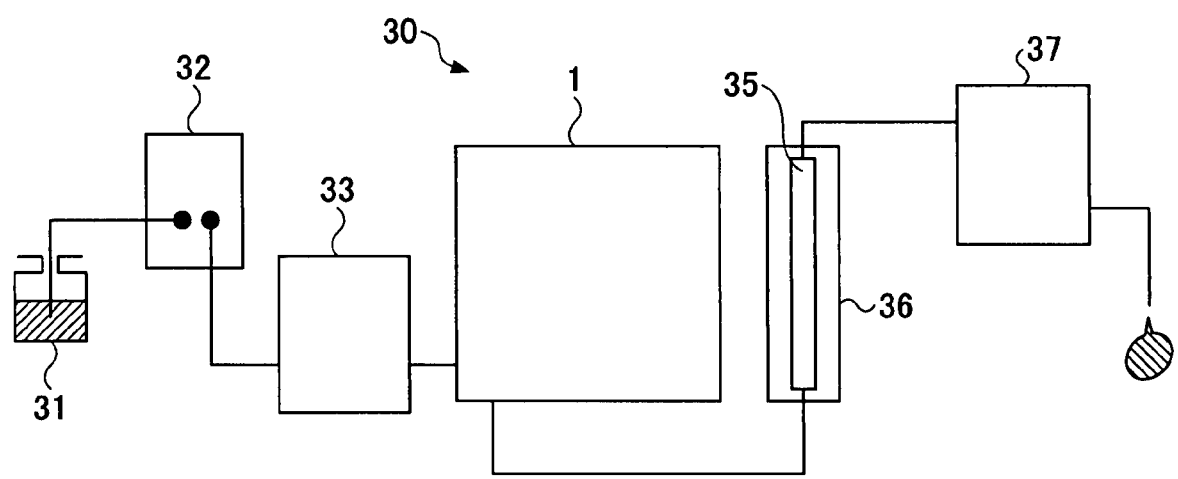
FIG. 3 is a schematic diagram illustrating a liquid chromatograph including the sample injection device according to an embodiment of the present invention.

FIG. 2 is a perspective view illustrating a configuration of a sample injection device 1 according to an embodiment of the present invention. FIG. 3 is a block diagram illustrating a configuration of a liquid chromatograph 30 including the sample injection device 1. The configuration of the liquid chromatograph 30 is described first with reference to FIG. 3.

The liquid chromatograph 30 includes a mobile phase reservoir 31 for holding a liquid used as a mobile phase, a mobile phase deaerator 32 for removing air from the liquid mobile phase, a pump 33 (that corresponds to a mobile phase supplying unit described in claims) for feeding the liquid mobile phase from the mobile phase reservoir 31 to a detector 37, a sample injection device 1 for injecting a sample into the liquid mobile phase being sent to a separation column 35, the separation column 35 filled with a filler for separating components of the sample, a constant-temperature bath 36 for maintaining the separation column 35 at a constant temperature, and the detector 37 for detecting eluted components of the sample. The mobile phase is fed by the pump 33 from the mobile phase reservoir 31 via the sample injection device 1 to the separation column 35. The mobile phase is preferably supplied to the separation column 35 continuously so that sample analysis can be performed stably.

Figure 4:
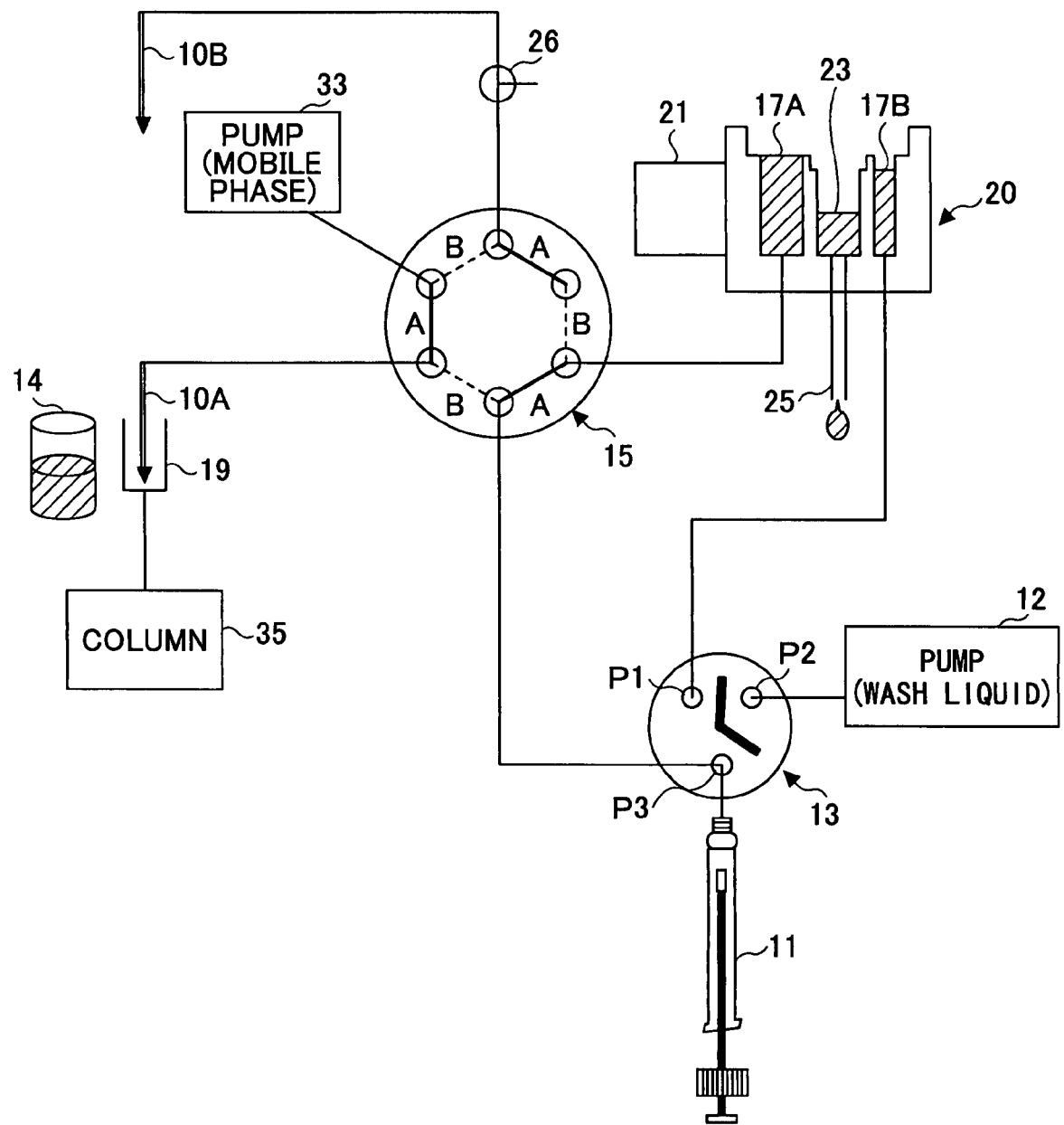
FIG. 4 is a drawing used to describe a preparatory step of an exemplary sample injection method using the sample injection device according to an embodiment of the present invention.

Next, the configuration of the sample injection device 1 is described with reference to FIGS. 2 and 4. FIG. 4 shows how the components of the sample injection device 1 are connected. The sample injection device 1 includes first and second sample injection needles 10A and 10B, a syringe 11 (that corresponds to a sample-suctioning unit described in claims), a wash liquid pump 12, a valve 13, a sample container 14, an injection valve 15, a wash liquid container 18, a cleaning device 20, and a needle moving unit (not shown)

The sample injection device 1 of this embodiment is characterized by having two sample injection needles 10A and 10B. The first sample injection needle 10A can be connected to the syringe 11 via the injection valve 15 and the valve 13. Also, the first sample injection needle 10A can be connected to the pump 33 via the injection valve 15.

When the first sample injection needle 10A is connected to the syringe 11 by switching the valves 13 and 15, a sample can be drawn into or withdrawn from the first sample injection needle 10A by pulling or pushing the piston of the syringe 11. When the injection valve 15 is switched and the first sample injection needle 10A is connected via the injection valve 15 to the pump 33, a mobile phase is fed by the pump 33 to the first sample injection needle 10A.

The second sample injection needle 10B can also be connected to the pump 33 via the injection valve 15. When the injection valve 15 is switched and the second sample injection needle 10B is connected via the injection valve 15 to the pump 33, the mobile phase is fed by the pump 33 into the second sample injection needle 10B.

A drip-preventing three-way solenoid valve 26 is provided in the path of piping connecting the second sample needle 10B and the injection valve 15. The drip-preventing three-way solenoid valve 26 closes when the second sample injection needle 10B is not attached to an injection port 19 but, for example, is being moved and the injection valve 15 is switched to a connection mode B shown in FIG. 4, and thereby prevents the mobile phase from flowing out of the second needle 10B.

The wash liquid container 18 contains a wash liquid and is connected to the wash liquid pump 12 (the wash liquid container 18 is not shown in FIG. 4). The wash liquid in the wash liquid container 18 is drawn in and pumped into the valve 13 by the wash liquid pump 12.

The valve 13 selectively supplies the wash liquid fed from the wash liquid container 18 by the wash liquid pump 12 to the cleaning device 20 or the first sample injection needle 10A. More specifically, the valve 13 includes three ports P1 through P3 two of which can be selectively connected.

The syringe 11 and the injection valve 15 are both connected to the port P3 of the valve 13. In other words, the syringe 11 and the injection valve 15 are always connected. Also, the valve 13 can be switched to a connection mode where no pair of the ports P1 through P3 is connected to each other.

The cleaning device 20 includes cleaning units 17A and 17B, an ultrasonic transducer 21, a waste liquid port 23, and waste liquid piping 25. When the valve 13 is switched and the cleaning device 20 is connected to the wash liquid pump 12, a wash liquid (water is used in this embodiment) is supplied to the cleaning device 20 from the wash liquid container 18. Excess wash liquid flows into the waste liquid port 23 and is discharged as waste liquid from the waste liquid piping 25 connected to the waste liquid port 23.

As described later, the cleaning device 20 washes away a sample adhering to the first sample injection needle 10A inserted therein and thereby prevents carry-over. The ultrasonic transducer 21 provided in the cleaning device 20 enables cleaning the first sample injection needle 10A using ultrasound. This configuration improves the effectiveness of cleaning the first sample injection needle 10A and thereby makes it possible to more effectively prevent carry-over.

The injection port 19 is connected to the separation column 35. In the sample injection device 1 of this embodiment, the injection port 19 is not connected to but completely separated from the injection valve 15. As described later, the first sample injection needle 10A containing a sample drawn therein is attached to the injection port 19 and the sample is ejected into the injection port 19. The sample is then carried by the flow of a mobile phase to the separation column 35.

The injection valve 15 has six ports to which the first sample injection needle 10A, the second sample injection needle 10B, the valve 13, the pump 33, and the cleaning device 20 are connected. The injection valve 15 switches between a connection mode indicated by solid lines A in FIG. 4 (hereafter called the connection mode A) and a connection mode indicated by broken lines B in FIG. 4 (hereafter called the connection mode B).

When the injection valve 15 is in the connection mode A, the first sample injection needle 10A is connected via the injection valve 15 to the pump 33 and the valve 13 is connected via the injection valve 15 to the cleaning unit 17A of the cleaning device 20. In this mode, the second sample injection needle 10B is disconnected from other components. When the injection valve 15 is in the connection mode B, the first sample injection needle 10A is connected via the injection valve 15 to the valve 13 and the second sample injection needle 10B is connected via the injection valve 15 to the pump 33.

Operations of the sample injection device 1 configured as described above and a sample injection method of injecting a sample into the separation column 35 using the sample injection device 1 are described below with reference to FIGS. 4 through 9.

FIG. 4 shows the sample injection device 1 performing a preparatory step (first step) before drawing a sample into the first sample injection needle 10A. In the preparatory step, the injection valve 15 is in the connection mode A and no pair of the ports P1 through P3 of the valve 13 is connected to each other. The first sample injection needle 10A is attached to the injection port 19 by the needle moving unit (not shown).

The second sample injection needle 10B is placed by the needle moving unit in a waiting position near the injection port 19. In other words, in the preparatory step, the second sample injection needle 10B is disconnected and is not used. Also, the drip-preventing three-way solenoid valve 26 is closed to block the piping connecting the second sample needle 10B and the injection valve 15.

Accordingly, in the preparatory step, a mobile phase from the pump 33 is fed into the separation column 35 via the first sample injection needle 10A and the injection port 19.

Figure 5:
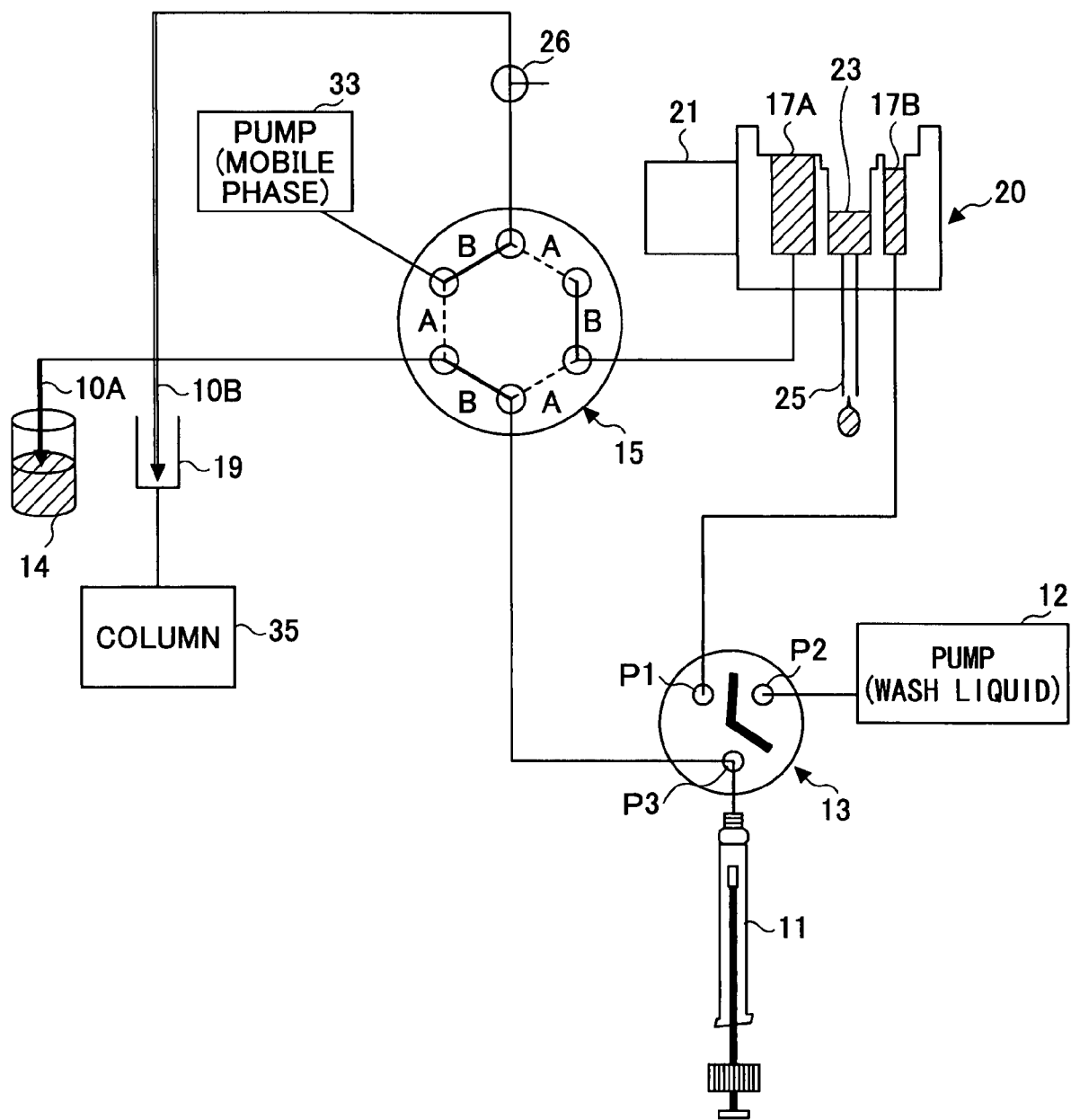
FIG. 5 is a drawing used to describe a sample-suctioning step of the exemplary sample injection method using the sample injection device according to an embodiment of the present invention.

FIG. 5 shows a sample-suctioning step (second step) of drawing a sample into the first sample injection needle 10A. In the sample-suctioning step, the first sample injection needle 10A is inserted into the sample container 14 by the needle moving unit and the second sample injection needle 10B is attached to the injection port 19 in place of the first sample injection needle 10A. The injection valve 15 is switched to the connection mode B. Also, the drip-preventing three-way solenoid valve 26 is opened to connect the second sample injection needle 10B and the injection valve 15.

Accordingly, in the sample-suctioning step, the mobile phase from the pump 33 is fed into the separation column 35 via the second sample injection needle 10B and the injection port 19. In other words, even when the second sample injection needle 10B is attached to the injection port 19 in place of the first sample injection needle 10A, the mobile phase is constantly fed into the separation column 35. This configuration makes it possible to stably perform sample analysis.

Meanwhile, the first sample injection needle 10A is connected to the syringe 11 via the injection valve 15 and the valve 13. The sample in the sample container 14 is drawn into the first sample injection needle 10A by operating the syringe 11. The amount of the sample drawn into the first sample injection needle 10A is predetermined such that the sample does not flow into the injection valve 15. This also prevents a sample from adhering to the inner surface of the injection valve 15 and makes it possible to prevent carry-over. The first sample injection needle 10A may have a sample loop to increase the amount of sample that can be drawn into the needle.

Figure 6:
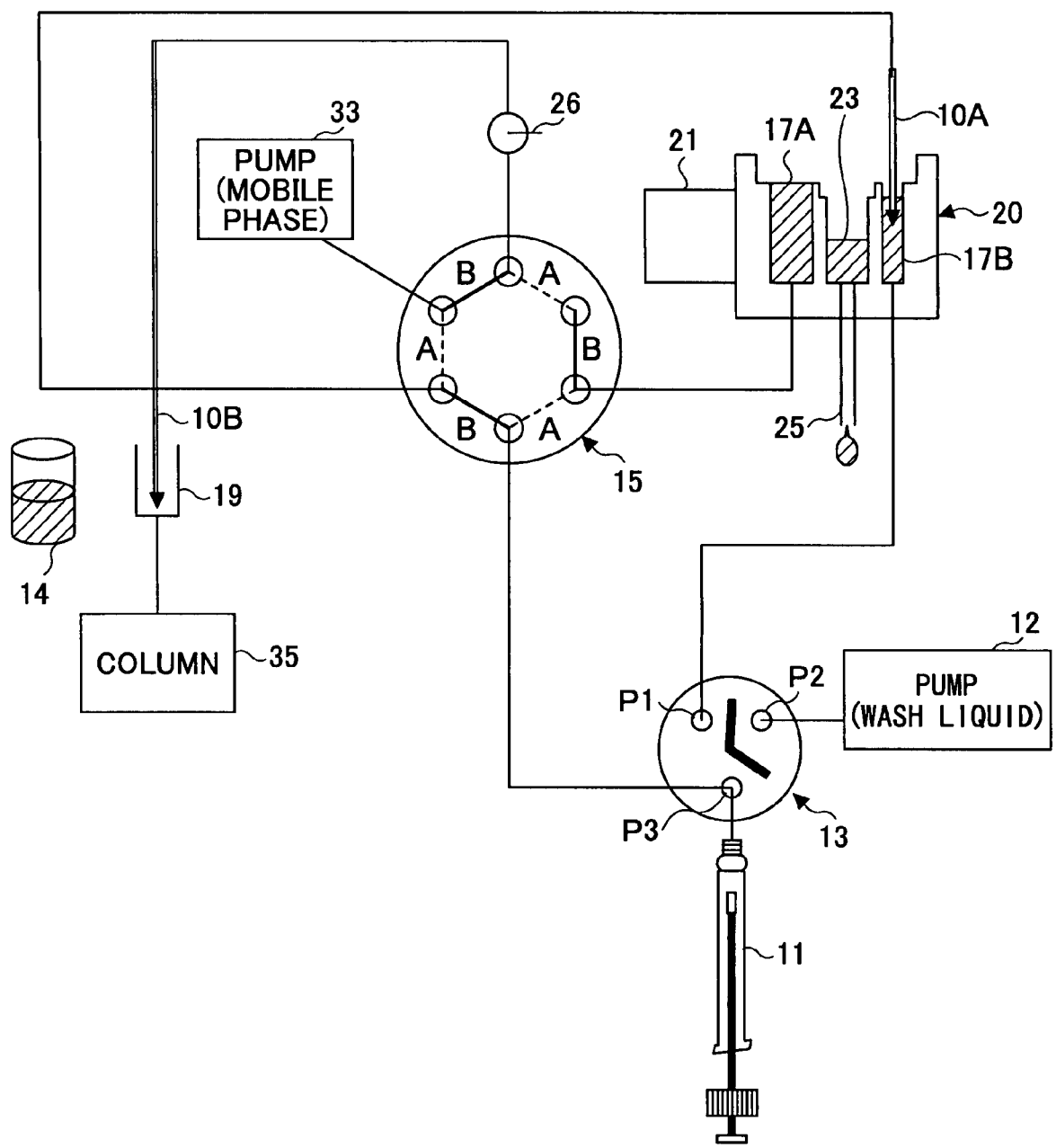
FIG. 6 is a drawing used to describe a pre-cleaning step of the exemplary sample injection method using the sample injection device according to an embodiment of the present invention where a sample injection needle is pre-cleaned.
Figure 7:
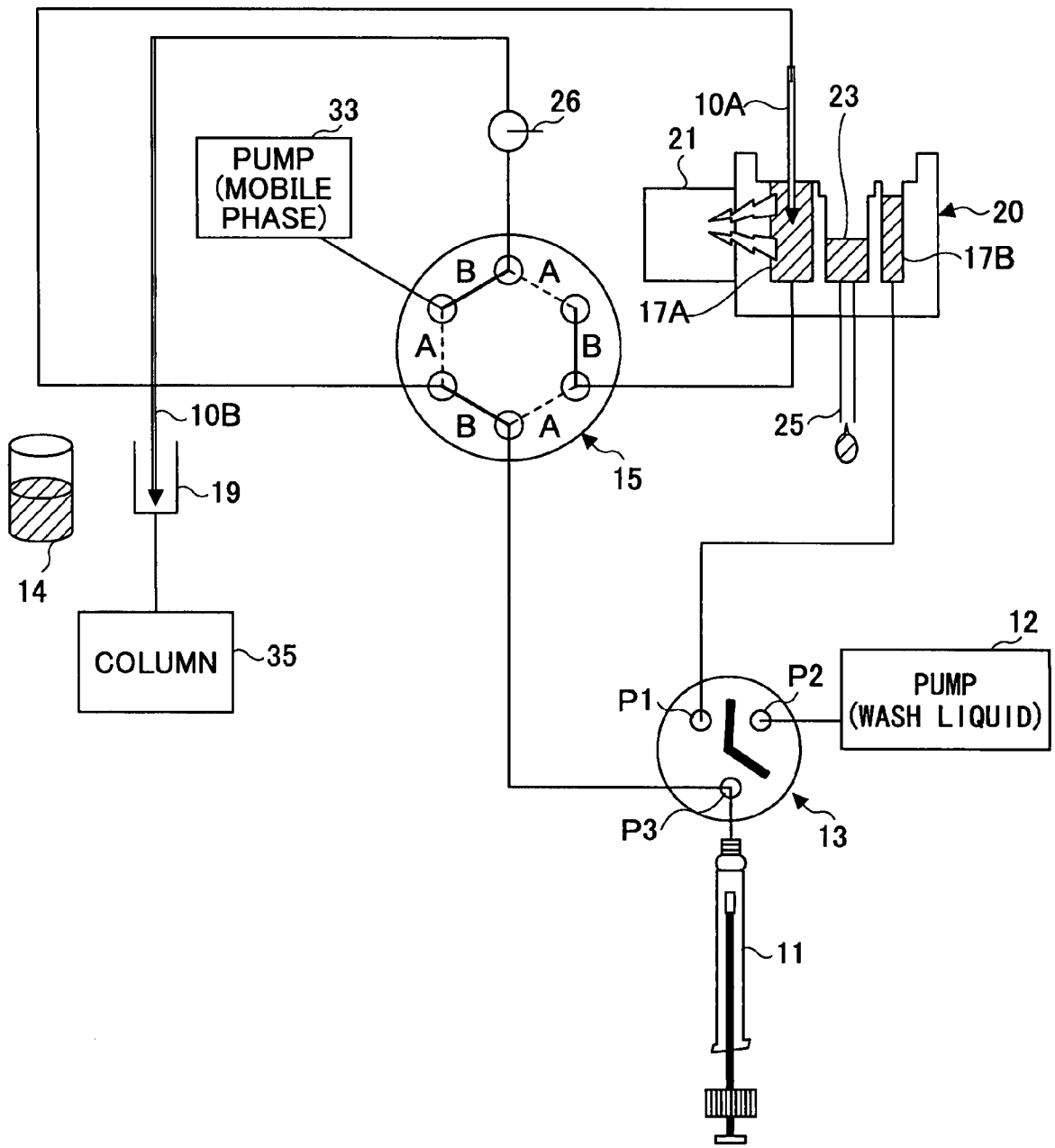
FIG. 7 is a drawing used to describe an ultrasonic-cleaning step of the exemplary sample injection method using the sample injection device according to an embodiment of the present invention where a sample injection needle is ultrasonically cleaned.

FIGS. 6 and 7 show cleaning steps of washing away a sample that adheres to the outer surface of the first sample injection needle 10A when the needle is dipped into the sample in the sample container 14. FIG. 6 shows a pre-cleaning step for roughly washing away a sample adhering to the outer surface of the first sample injection needle 10A. FIG. 7 shows an ultrasonic-cleaning step for more completely washing away a sample adhering to the outer surface of the first sample injection needle 10A.

In the pre-cleaning step shown in FIG. 6, the injection valve 15 is kept in the connection mode B and the first sample injection needle 10A is inserted by the needle moving unit into the cleaning unit 17B of the cleaning device 20. The valve 13 is switched to connect the port P1 and Port P2 and thereby to supply the wash liquid in the wash liquid container 18 via the wash liquid pump 12 to the cleaning unit 17B. As a result, the wash liquid gushes into the cleaning unit 17B and pre-cleans the outer surface of the first sample injection needle 10A. The wash liquid overflowing the cleaning unit 17B is discharged via the waste liquid port 23-and the waste liquid piping 25.

In the subsequent ultrasonic-cleaning step shown in FIG. 7, the injection valve 15 is kept in the connection mode B and the first sample injection needle 10A is inserted by the needle moving unit into the cleaning unit 17A of the cleaning device 20. The valve 13 is switched to a connection mode where no pair of the ports P1 through P3 is connected to each other. Then, the ultrasonic transducer 21 is driven to generate ultrasound. The wash liquid in the cleaning unit 17A is vibrated by the ultrasound and the sample adhering to the outer surface of the first sample injection needle 10A is sufficiently washed away. Even during the above cleaning steps, the mobile phase from the pump 33 is continuously fed into the separation column 35 via the injection valve 15, the second sample injection needle 10B, and the injection port 19.

Figure 8:
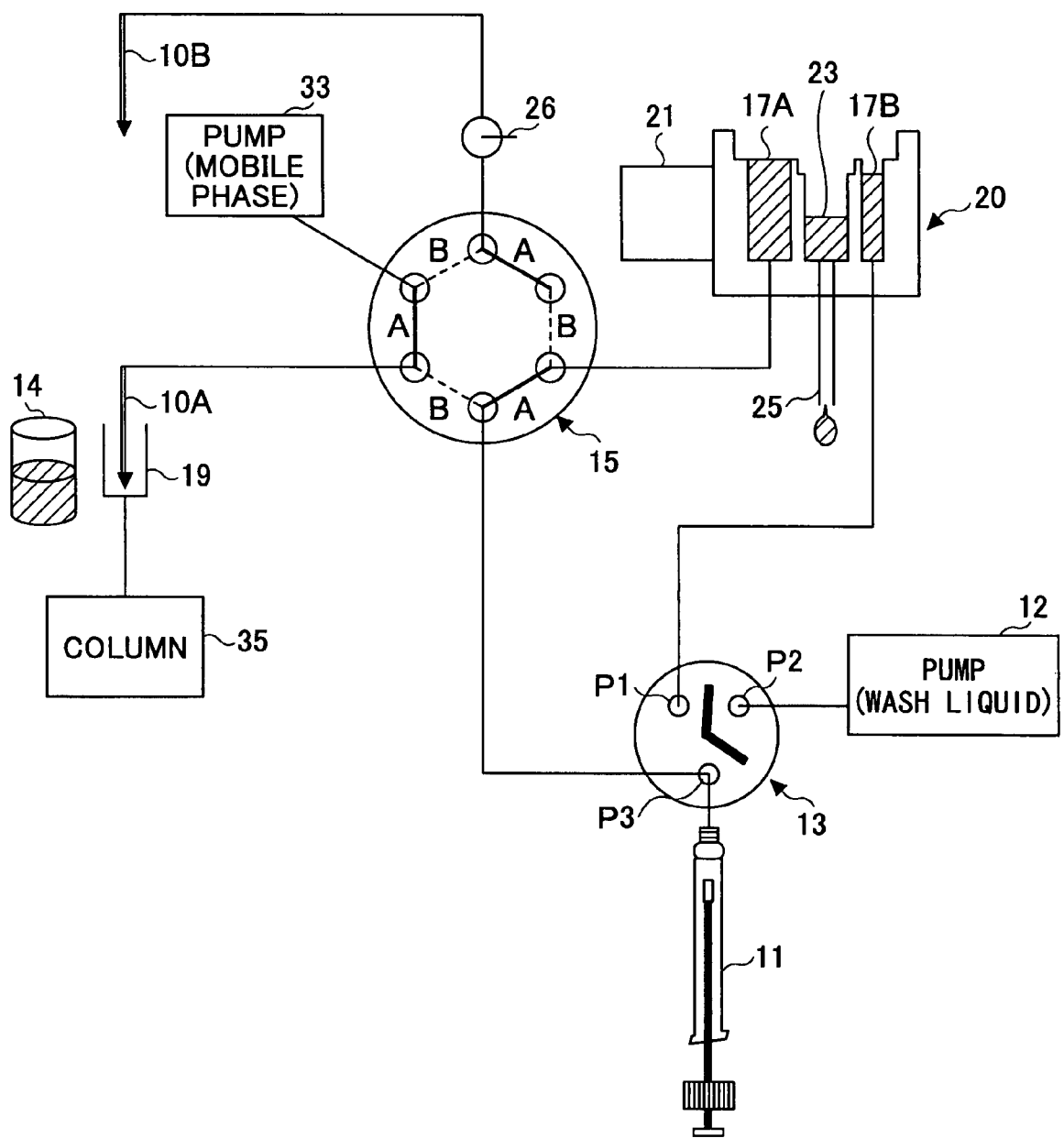
FIG. 8 is a drawing used to describe a sample analysis step of the exemplary sample injection method using the sample injection device according to an embodiment of the present invention (1)

After the cleaning steps, the sample in the first sample injection needle 10A is fed into the separation column 35. FIG. 8 shows a sample feeding step (third step) of feeding the sample into the separation column 35.

In the sample feeding step, the injection valve 15 is switched again from the connection mode B to the connection mode A and the first sample injection needle 10A is attached again to the injection port 19. The second sample injection needle 10B is moved by the needle moving unit to a waiting position near the injection port 19.

When the second sample injection needle 10B is moved, the drip-preventing three-way solenoid valve 26 is closed to block the piping connecting the second sample needle 10B and the injection valve 15. Also, in the sample feeding step (third step), the first sample injection needle 10A containing the drawn-in sample is attached to the injection port 19 and connected by the injection valve 15 to the pump 33.

With this configuration, the sample in the first sample injection needle 10A is fed into the separation column 35 without going through the injection valve 15. Components of the sample fed into the separation column 35 are separated and sent to the detector 37 for analysis.

Thus, unlike a conventional device and method, the sample injection device 1 and a sample injection method of this embodiment make it possible to effectively prevent a sample from remaining in the injection valve 15 and thereby to effectively prevent carry-over. Also, preventing carry-over in the sample injection device 1 makes it possible to increase the number of theoretical plates.

Figure 9:
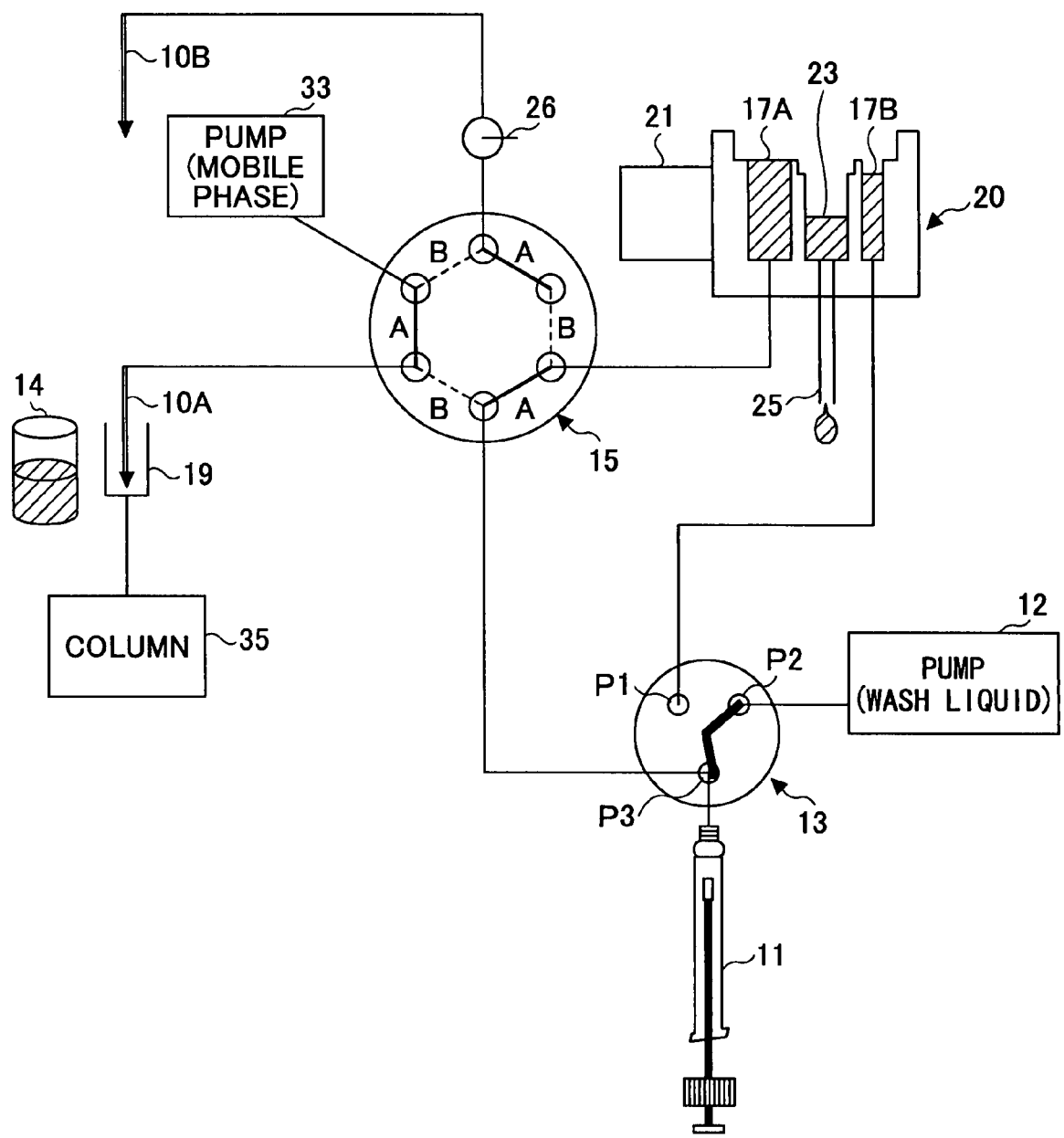
FIG. 9 is a drawing used to describe the sample analysis step of the exemplary sample injection method using the sample injection device according to an embodiment of the present invention (2)

By the way, the wash liquid in the cleaning unit 17A may be renewed during the above sample feeding step (or during the sample analysis). In this case, as shown in FIG. 9, the valve 13 is switched to connect the ports P2 and P3 and thereby to supply the wash liquid in the wash liquid container 18 to the cleaning unit 17A of the cleaning device 20 via the wash liquid pump 12, the valve 13, and the injection valve 15.

With the new supply of the wash liquid, the contaminated wash liquid used for cleaning the first sample injection needle 10A is discharged via the waste liquid port 23 and the waste liquid piping 25, and the cleaning unit 17A is filled with a clean, non-contaminated wash liquid. This configuration makes it possible to effectively wash away the sample adhering to the outer surface of the first sample injection needle 10A and thereby to prevent carry-over resulting from the remaining sample on the first sample injection needle 10A.

EXAMPLE 1

Results of carry-over evaluation tests performed on the liquid chromatograph 1 of the present invention are described below with reference to FIGS. 10 and 11.

Carry-over evaluation tests were performed using the liquid chromatograph 30 shown in FIG. 3 including the sample injection device 1 shown in FIGS. 2 and 4. In the evaluation tests shown in FIG. 10, a mixed solvent of $CH_3OH$ and $H_2O$ (volume ratio 70:30) was used as the mobile phase for liquid chromatography. In the evaluation tests shown in FIG. 11, a mixed solvent of 10 mM of $NH_4H_2PO_4$ containing 100 mM of $Na_2ClO_4$ (pH2.6) and CH3CN (volume ratio 55:45) was used as the mobile phase for liquid chromatography. The flow speed of the solvents used as the mobile phases were 200 μl/min. Water was used as the wash liquid.

Figure 11:
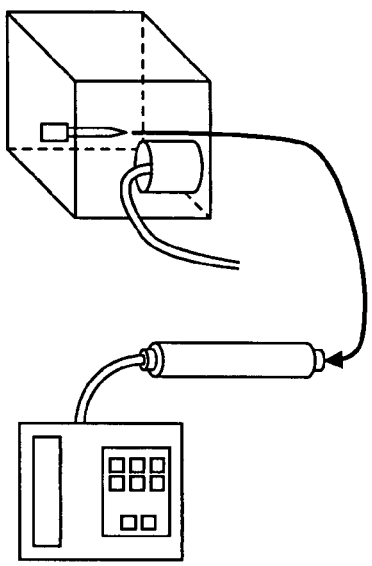
FIG. 11 is a table used to describe advantageous effects of the present invention (2).
Figure 11:
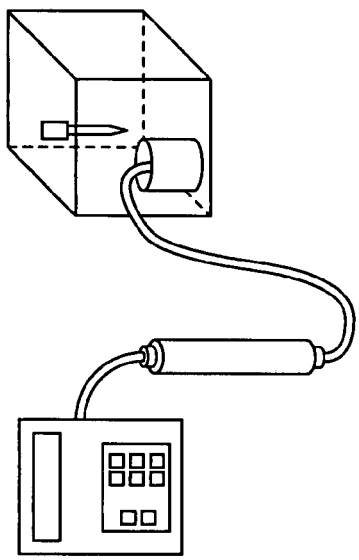

In the evaluation tests shown in FIGS. 10 and 11, columns having the same dimensions of 2 mm (inner diameter)×150 mm (length) were used as the separation column 35 of the example and the separation column 105 of the comparative example. The separation column 35 was maintained at a temperature of 40° C. using the constant-temperature bath 36. In both the example and the comparative example, octadecyl silica gel having a particle diameter of five μm was used as the column filler or the stationary phase for liquid chromatography. As samples for evaluating carry-over, uracil was used in the evaluation tests shown in FIG. 10 and basic and hydrophobic chlorhexidine that is highly likely to cause carry-over was used in the evaluation tests shown in FIG. 11. As a detector, an absorptiometer using ultraviolet rays with a wavelength of 254 nm was used.

The example in FIG. 10 shows the results of an evaluation test performed using the sample injection device 1 of this embodiment where a sample drawn into the first sample injection needle 10A is directly fed into the separation column 35 without going through the injection valve 15. The comparative example in FIG. 10 shows the results of an evaluation test performed using the conventional injection device (see FIG. 1) where a sample drawn into the sample injection needle 100 is fed into the separation column 105 through the injection valve 115.

In the comparative example, as shown in FIG. 10, the 5% peak width was 0.2374 and the number of theoretical plates was 7659. In the example, the 5% peak width was 0.2201 and the number of theoretical plates was 8686, which is about 1000 plates larger than that of the comparative example. As described above, in the comparative example and the example, the same column and the same column filler were used and the amounts of the injected sample were also the same. Therefore, the test results indicate that peaks appear sharper and separation can be performed more accurately with the sample injection device 1 of this embodiment than with the conventional sample injection device.

In each of the evaluation tests shown in FIG. 11, first through sixth measuring steps were performed. In the first measuring step, chlorhexidine was used as the sample. In the second through sixth measuring steps, only the mobile phase was fed into the column without injecting the sample (chlorhexidine). Other conditions were the same as in the evaluation tests shown in FIG. 10. More specifically, the peak area (S1) of a peak detected in the first measuring step, where a sample was injected, was measured. Next, among the second through sixth measuring steps where only the mobile phase was fed into the column, the peak area (S2) of a peak detected in the second measuring step was measured and the proportion of the peak area S2 to the peak area S1 (S2/S1) was calculated.

FIG. 11 shows the results of evaluation tests performed using the conventional injection device (comparative example) in comparison with the results of evaluation tests performed using the sample injection device 1 of this embodiment (example). Theoretically, it is expected that no peak is detected in the second and subsequent measuring steps. Therefore, a smaller proportion of the peak area S2 to the peak area S1 (hereafter called the peak area proportion) indicates that carry-over is reduced more effectively.

As shown in FIG. 11, the average of peak area proportions (S2/S1) obtained in four evaluation tests in the comparative example was 0.0020, and the average of peak area proportions (S2/S1) obtained in four evaluation tests in the example was 0.0009. Thus, the average peak area proportion of the example was much smaller than that of the comparative example. As the test results in FIG. 10 show, the sample injection device 1 and the sample injection method of this embodiment make it possible to reduce carry-over and thereby to improve the accuracy of sample analysis by the liquid chromatograph 30 including the sample injection device 1.

The present international application is based on Japanese Priority Application No. 2005-015583 filed on Jan. 24, 2005, the entire contents of which are hereby incorporated herein by reference.

The invention claimed is:

1. A sample injection device, comprising:
a sample injection port connected to a column;
a mobile phase supplying unit configured to supply a mobile phase;
a first sample injection needle attachable to the sample injection port;
a second sample injection needle attachable to the sample injection port;
a sample-suctioning unit connectable to the first sample injection needle and configured to draw a sample into the first sample injection needle when connected thereto; and
a switching valve configured to selectively connect the first sample injection needle to the mobile phase supplying unit or the sample-suctioning unit and to connect the second sample injection needle to the mobile phase supplying unit;
wherein the switching valve is
configured to connect the first sample injection needle to the mobile phase supplying unit when the first sample injection needle is attached to the sample injection port, and
configured to connect the first sample injection needle to the sample-suctioning unit and to connect the second sample injection needle to the mobile phase supplying unit when the second sample injection needle is attached to the sample injection port.

2. The sample injection device as claimed in claim 1, further comprising:
a valve disposed in a path of piping connecting the second sample injection needle and the switching valve and configured to block the piping when the second sample injection needle is detached from the sample injection port.

3. A method of injecting a sample into a column using the sample injection device as claimed in claim 1, comprising:
a first step of attaching the first sample injection needle to the sample injection port, connecting the first sample injection needle via the switching valve to the mobile phase supplying unit, and disconnecting the second sample injection needle;
a second step of drawing the sample into the first sample injection needle by connecting the first sample injection needle via the switching valve to the sample-suctioning unit, attaching the second sample injection needle to the sample injection port, and connecting the second sample injection needle via the switching valve to the mobile phase supplying unit; and
a third step of attaching the first sample injection needle to the sample injection port, feeding the sample drawn into the first sample injection needle into the column by connecting the first sample injection needle via the switching valve to the mobile phase supplying unit, and disconnecting the second sample injection needle.

4. A method of injecting a sample into a column using the sample injection device as claimed in claim 1, comprising:
a first step of attaching the first sample injection needle to the sample injection port, connecting the first sample injection needle via the switching valve to the mobile phase supplying unit, and disconnecting the second sample injection needle;
a second step of drawing the sample into the first sample injection needle by connecting the first sample injection needle via the switching valve to the sample-suctioning unit, attaching the second sample injection needle to the sample injection port, and connecting the second sample injection needle via the switching valve to the mobile phase supplying unit; and
a third step of attaching the first sample injection needle to the sample injection port, feeding the sample drawn into the first sample injection needle into the column by connecting the first sample injection needle via the switching valve to the mobile phase supplying unit, and disconnecting the second sample injection needle; wherein
a valve is provided in a path of piping connecting the second sample injection needle and the switching valve; and
the piping is blocked by the valve in the first step and the third step.

5. A liquid chromatograph, comprising:

a sample injection port connected to a column;

a mobile phase supplying unit configured to supply a mobile phase;

a first sample injection needle attachable to the sample injection port;

a second sample injection needle attachable to the sample injection port;

a sample-suctioning unit connectable to the first sample injection needle and configured to draw a sample into the first sample injection needle when connected thereto;

a switching valve configured to selectively connect the first sample injection needle to the mobile phase supplying unit or the sample-suctioning unit and to connect the second sample injection needle to the mobile phase supplying unit;

a separation column into which the mobile phase and the sample are fed from the first sample injection needle and which is configured to separate components of the sample; and a detector configured to detect the components of the sample separated by the separation column;

wherein the switching valve is configured to connect the first sample injection needle to the mobile phase supplying unit when the first sample injection needle is attached to the sample injection port, and configured to connect the first sample injection needle to the sample-suctioning unit and to connect the second sample injection needle to the mobile phase supplying unit when the second sample injection needle is attached to the sample injection port.

* * * * *